United States Patent [19]
Pottash

[11] Patent Number: 5,644,438
[45] Date of Patent: Jul. 1, 1997

[54] OPTICAL DEVICE FOR VIEWING INTO RESTRICTED AREAS

[76] Inventor: Paul C. Pottash, 1414 Dorset La., Wynnewwod, Pa. 19096

[21] Appl. No.: 550,013

[22] Filed: Oct. 30, 1995

[51] Int. Cl.[6] ............... G02B 27/02; F21V 33/00; A61B 1/06
[52] U.S. Cl. .............. 359/798; 359/367; 359/726; 362/109; 362/138; 600/170; 600/179
[58] Field of Search .................. 359/367, 798, 359/726; 362/109, 138, 208, 268; 600/160, 168, 170, 179

[56] References Cited

U.S. PATENT DOCUMENTS

| | | |
|---|---|---|
| 849,570 | 4/1907 | Pino . |
| 1,260,341 | 3/1918 | Curtis . |
| 1,292,326 | 1/1919 | Jacobson . |
| 1,814,540 | 7/1931 | Bander . |
| 1,884,968 | 10/1932 | Bloch . |
| 2,092,672 | 9/1937 | Hyatt ............................ 88/39 |
| 2,285,987 | 6/1942 | Krimsky ......................... 88/20 |
| 2,326,343 | 8/1943 | Eichenberger .................. 88/39 |
| 2,396,440 | 3/1946 | Schmidt ......................... 88/39 |
| 2,423,267 | 7/1947 | Strang ........................... 88/57 |
| 2,503,850 | 4/1950 | Smith et al. ................... 88/39 |
| 2,778,267 | 1/1957 | Miller, Jr. ..................... 88/14 |
| 3,178,994 | 4/1965 | Lang ............................ 359/367 |
| 3,595,220 | 7/1971 | Kawahara ....................... 128/6 |
| 4,120,563 | 10/1978 | Stafanou . |
| 4,195,904 | 4/1980 | Yamashita ..................... 359/367 |
| 4,815,816 | 3/1989 | Schneider . |
| 5,398,672 | 3/1995 | Carothers et al. ............. 128/22 |

Primary Examiner—Paul M. Dzierzynski
Assistant Examiner—Mark Robinson
Attorney, Agent, or Firm—Synnestvedt & Lechner

[57] ABSTRACT

An optical device for illuminating and inspecting the interior of restricted spaces at a distance, comprising an elongated tubular housing having a distal end, a proximal sight end, and two apertures adjacent to the distal end and on the outer surface of the housing, namely, a first aperture through which a focused light beam reflected off of a first mirror is directed into a restricted space, and a second aperture through which reflected light and the image within the restricted space is received and reflected off of a second mirror through the sight end.

18 Claims, 4 Drawing Sheets

OPTICAL DEVICE FOR VIEWING INTO RESTRICTED AREAS

BACKGROUND OF THE INVENTION

This invention relates to optical devices for illuminating and inspecting the interior of restricted spaces and, more particularly, restricted spaces at a distance.

Numerous devices have been proposed and used for inspecting spaces and/or compartments which are confined in space and/or to which access is difficult or even dangerous. Such devices typically involve the use of any number of combinations of lenses, magnifiers, mirrors, and/or light sources in order to help make the visual field larger, clearer and/or brighter. However, to date, various difficulties have arisen with the devices known in the art—difficulties ranging from insufficient focus, lack of sufficient light or properly directed or focused light, excess or diffused illumination resulting in lack of clarity and reduction of visual contrast, to the inability to adequately access particularly restricted spaces. Furthermore, an adequate device has yet to be disclosed which provides for the illumination and the inspection of restricted areas or objects at a distance, denoted hereinafter as "telescopic inspection."

Early prior art optical devices include various devices which combine a reading glass or magnifying lens with a separate light source supplied adjacent to the lens, so as to illuminate the object or area being viewed through the lens. Examples of such devices are disclosed in U.S. Pat. Nos. 1,814,540 to Bander, 1,884,968 to Bloch, 2,092,672 to Hyatt and 2,503,850 to Smith et al. While these patents each disclose a lens and illumination combination, none provide a system whereby restricted areas or spaces can be accurately viewed, due to the inadequate size and/or configuration of such devices.

Attempts to satisfy such a need have led to the utilization of reflective viewing apparatus comprising reflective surfaces or mirrors, together with a lens and illumination combination, such as that disclosed in U.S. Pat. No. 4,120,563 to Stefanou. However, while these devices may provide for the inspection of objects or areas in a different field of view, they still do not adequately provide for access to confined or restricted areas, and certainly none have provided for the adequate inspection of narrow spaces and/or objects, let alone visual fields at a distance within such narrow spaces.

U.S. Pat. No. 1,292,326 to Jacobson discloses an elongate device for inspecting confined areas, such as the interior of gas engines. This device optionally employs a mirrored attachment in combination with a magnifying lens and lamp; however, the attachment is disposed upon the device so that the rays emitted from the lamp are not directly projected upon the mirror. A significant drawback of this device, as with other similar inspection devices, is that the light is not aimed directly upon the object or area to be viewed. As a result, the illumination may be insufficient or there may be an abundance of misdirected illumination, which can result in lack of visual clarity. Furthermore, while attempts may be made to use the device for telescopic inspection, the resulting insufficient, misdirected, or excess illumination results in even less visual clarity due to the desired longer distance of inspection.

One apparent attempt to overcome the problem of diffused lighting is disclosed in U.S. Pat. No. 2,778,267 to Miller, Jr. A borescope is provided, wherein the light is reflected off of a primary reflective surface into the bore and the resulting image is reflected off of a secondary reflective surface through the lens in the borescope. It may be inferred that because the reflective surface used to project the light is separate from the reflective surface used to inspect the bore, and the resulting light beam is thus directed in a different optical plane than the viewed area, the incidence of diffused light interfering with the observation may be reduced, although such reasoning is not explicitly disclosed in the patent. However, there is only one aperture in the borescope and, thus, the lighting is still directed through the same opening through which the image of the viewed area or surface is received. As a result, there still remains the probable occurrence of surplus or excess illumination, as well as diffused light and scattered or unfocused light rays. Such a result would not necessarily pose a problem if the light did not have to travel far and the object or space to be viewed was relatively close, such as in the instance of viewing the inner surface of a bore, in which case such a configuration would be suitable. However, the possibility of diffused light or inaccurately and non-focused light rays increases with the distance at which inspection is desired, and such a configuration would in no way be suitable for accurate distance or telescopic inspection of any sort.

Thus, although the device disclosed in the Miller, Jr. patent utilizes a combination of light, separate reflective surfaces and the ability to observe confined areas, its abilities are limited to the microscopic inspection, or inspection at a close distance, of an object or surface, such as the inside of a rifle bore, and is not conducive to the telescopic inspection within any similarly restricted area.

Furthermore, the Miller, Jr. device is intended only for the lengthwise, rotational surface inspection of a bore, and the battery end of the device is sized so as to be inserted first into the restricted space. As a result, the battery is necessarily of a size small enough to fit inside a bore, and such a small battery can provide only a limited amount of power. Moreover, because the battery is located at the opposite end of the eye piece and, thus, the aperture for illuminating and viewing is located at least that far from the end to be inserted, the Miller, Jr. device does not lend itself to the inspection of spaces or areas having a depth limited to a distance shorter than that from the battery end to the illuminating/viewing aperture.

OBJECTS OF THE INVENTION

Accordingly, it is a principal objective of this invention to provide an optical device for the inspection of restricted areas and, in particular, for the inspection of areas at a distance, whereby adequate illumination is provided without the occurrence of diffused or unfocused light.

An additional objective of this invention is to provide such an optical device which is adapted to access and inspect restricted areas, the only accessible dimension of which is limited in depth, such as the interior of walls, yet which remains flexible in its usefulness.

It is still a further objective of this invention to provide such an optical device which is of a convenient size to store and carry, of simple yet sturdy construction, and which is relatively simple and inexpensive to manufacture.

Other objectives and advantages of this invention, more or less specific than those referred to above, will become apparent in the course of the following description of the invention.

SUMMARY OF THE INVENTION

The foregoing, along with other objectives, are achieved in accordance with the present invention by providing an optical device for illuminating and optically inspecting the interior of a restricted space, comprising an elongated tubular housing comprising a proximal sight end having an opening to which viewing means is to be applied, and a distal end; first and second apertures disposed in end to end relationship in the outer surface of said housing, the first aperture being an illumination aperture adjacent to said distal end, and the second aperture being a viewing aperture anterior to the first aperture; first and second reflecting means disposed within the housing, the reflecting means corresponding with and located beneath the first and second apertures, each being angularly disposed and positioned in substantially parallel planes, and each having a reflective surface facing the proximal end; and a light source capable of providing a beam of light and located between the first and second reflecting means, the first reflecting means being positioned to project the light beam in a light path from the light source through the illumination aperture into the restricted space, and the second reflecting means being positioned to project the illuminated image in an image path from the restricted space through the viewing aperture and through the sight end.

The device provides for the simple and effective inspection of restricted spaces, the access to which is limited. In preferred embodiments, such inspection is enhanced by a focused beam of light which is precisely directed into the restricted space, thus avoiding undesirable light diffusion. The tubular housing is sized to be inserted into the restricted area perpendicular to the desired visual field. The first reflecting means projects the precisely directed light beam through a first aperture and into the restricted space, so as to illuminate the space or objects located within that space. A second reflecting means is provided to project the reflected light, and thus the lighted image of the viewed area within that space, through a second aperture to the sight end of the device to which viewing means, such as the eye of an observer, is applied.

The light beam being directed into the restricted space is advantageously obstructed from the observer's view which is limited to the image directed from the second reflecting means. The device is thereby capable of accurately and effectively illuminating the restricted space and any objects therein while, at the same time, conveniently avoiding from the observer's viewpoint the undesirable interference from surplus or diffused light.

DETAILED DESCRIPTION OF THE INVENTION

Figure 1:
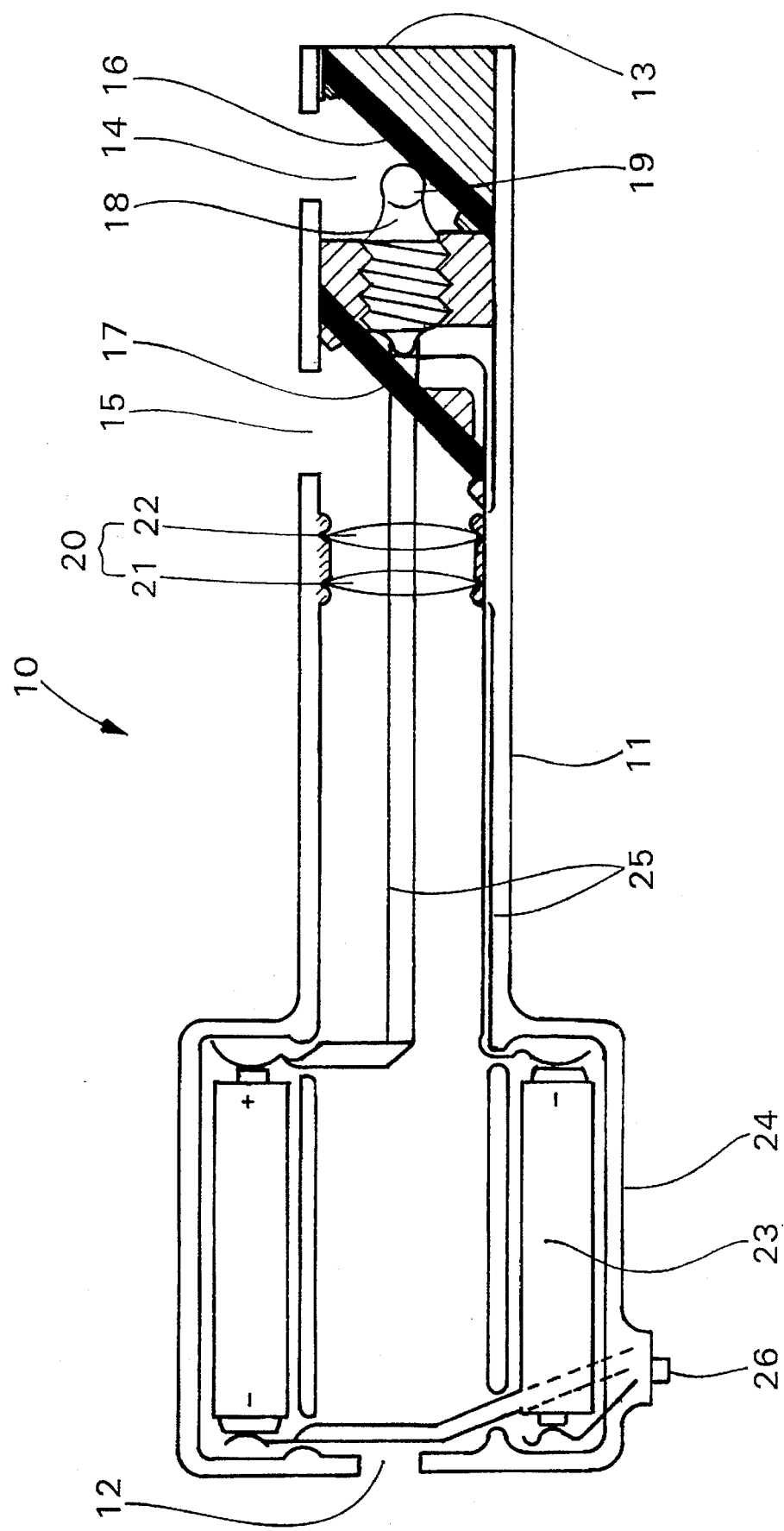
FIG. 1 is a sectional view of a preferred embodiment of the optical device of this invention.

The optical device of this invention importantly provides for the telescopic inspection of restricted spaces, the view of which is obstructed or hampered by the arrangement, design or alignment of the structure in which the space and any objects therein lie. For the purpose of convenience, the term "telescopic inspection" is used herein in a broad sense to refer to the viewing and inspection of spaces or objects at a distance.

In its broadest aspect, the optical device of this invention, as illustrated in the drawings, and designated generally as 10, comprises an elongated tubular housing 11 for inserting into a restricted space, the housing having a sight end 12 with an opening to which viewing means is applied, two apertures 14, 15 on its outer surface, a light source 18 and two light reflecting means preferably comprising mirrors 16, 17 in its interior. While the eye of an observer is the primary viewing means contemplated and referred to herein, it is to be understood that the sight end of this invention could equally be applied to the lens of a camera or other such viewing device if desired. Through the first aperture, which is the illumination aperture 14, the reflection of a beam of light passes in a light path from the light source 18 into the restricted space; and, through the second aperture, which is the viewing aperture 15, the light and the image illuminated thereby are received and projected in an image path from the restricted space through the sight end 12 to the eye of the observer or other viewing means.

Preferably, the mirrors 16, 17 are located beneath each aperture 14, 15, and the light source 18 is located between the mirrors so that when a light beam is provided by the light source, it is reflected off the first mirror 16, but such light is obstructed from the observer's view which is directed at the second mirror 17 beneath the viewing aperture 15, both of which are anterior to the light source 18 and illumination aperture 14.

The illumination aperture 15 and corresponding second mirror 17 are located adjacent to the distal end 13 of the optical device which is inserted into the restricted space, so as to provide for viewing restricted spaces having a limited depth, for example, those found within walls. The light source 18 is located immediately anterior to the first mirror 16 beneath the illumination aperture 14, such that the light being provided by the light source 18 is reflected and projected in a light path from the light source 18 through the illumination aperture 14 and into the restricted space. The viewing aperture 15 is a separate and distinct aperture from the illumination aperture 14. This arrangement of distinct and separate apertures has been found to eliminate the problem of surplus or scattered, misdirected light resulting in lack of clarity and reduction of visual contrast. A separate aperture 15 and mirror 17 are devoted solely to receiving and projecting the illuminated image in an image path from the restricted space to the eye of the observer, rather than merely one aperture being used to both direct the light and receive the reflected light and image.

Figure 2:
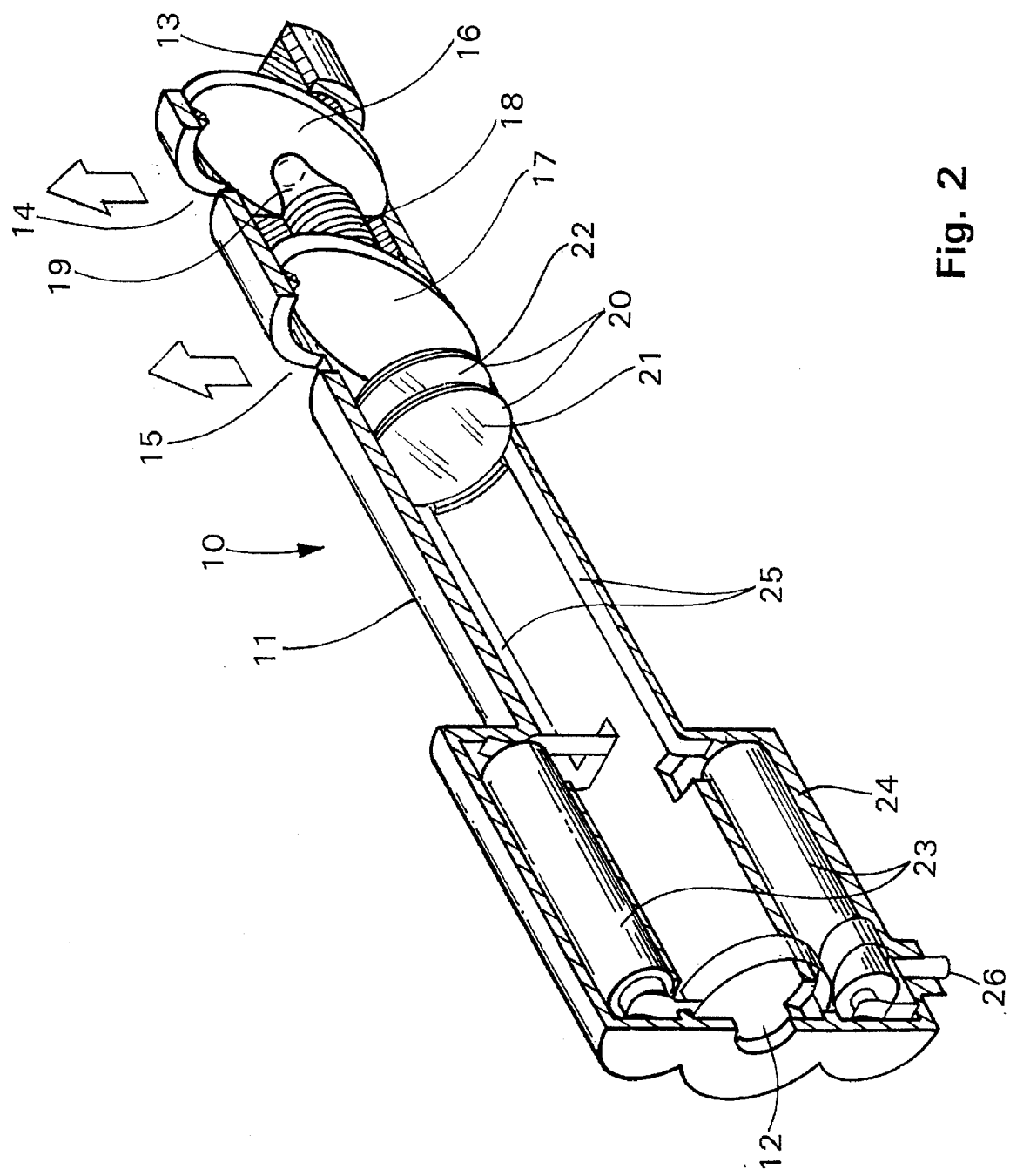
FIG. 2 is a schematic, perspective view of the optical device illustrated in FIG. 1.
Figure 3:
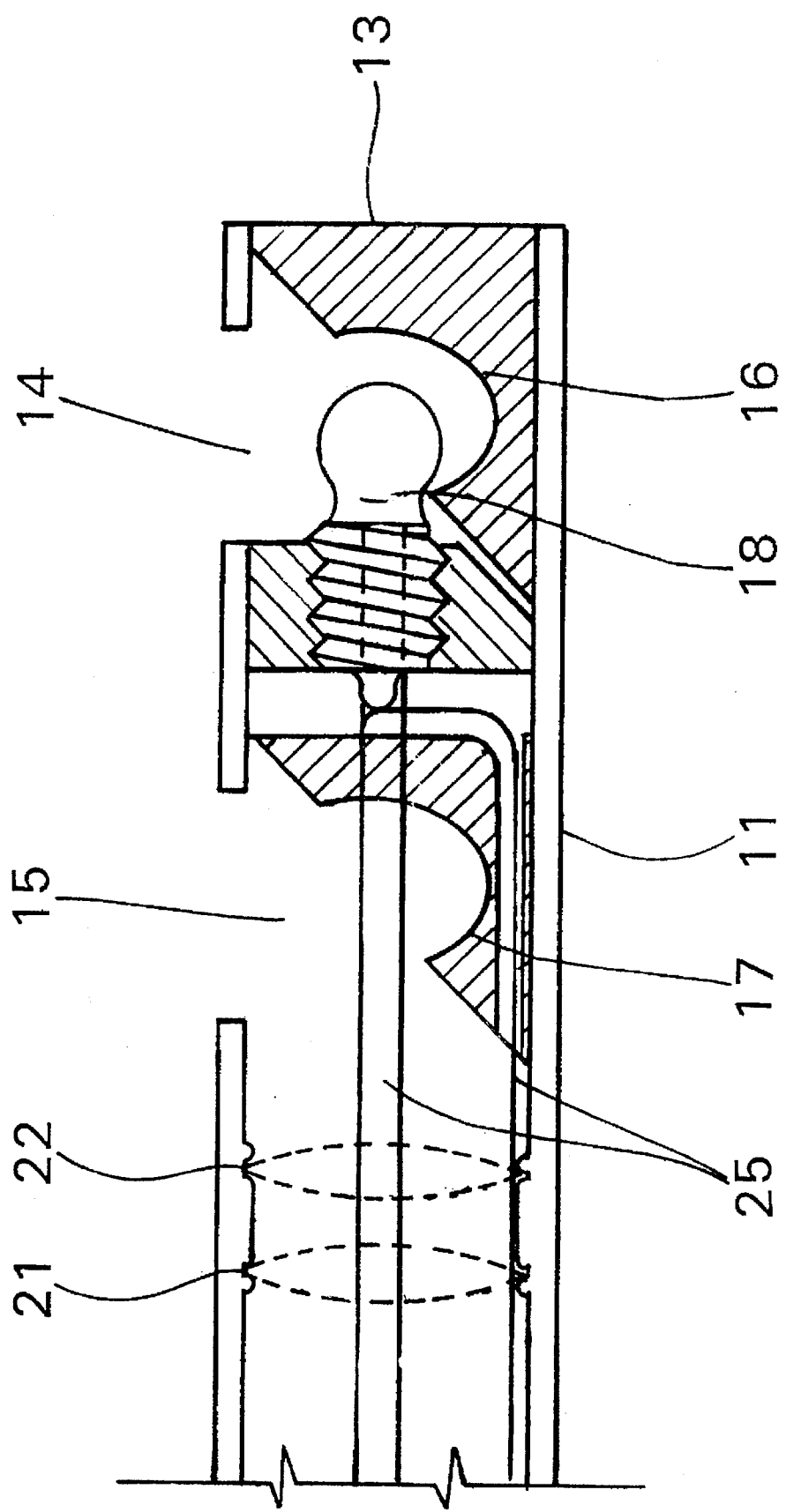
FIG. 3 is a partial sectional view of the subject optical device, illustrating an alternative embodiment with respect to the reflecting means.

Although various reflecting means are understood to be acceptable, including reflectors, such as reflective metallic surfaces, prisms, and mirrors, the preferred reflecting means of this invention are mirrors and, even more preferably, planar mirrors, as illustrated in FIGS. 1 and 2. The mirrors are angularly disposed and positioned in substantially parallel planes, the reflective surface of each facing the proximal sight end 12 of the instrument. In its simplest and preferred form, the optical device of this invention comprises first and second mirrors 16, 17 which have planar reflective surfaces and provide a direct and unaltered view of the object or space. However, as an alternative, the mirrors 16, 17 of this invention may have concave reflective surfaces, as shown in FIG. 3. It is contemplated that the use of such curved mirrors would provide a means for not only reflecting, but focusing the light beam in the light path and the illuminated image received in the image path. The mirrors are positioned so as to enable the inspection of the object or space which is out of alignment with and, in particular, at a position of about 90° relative to, the longitudinal axis of the device. Accordingly, the mirrors are preferably positioned at an angle of about 35° to 55° relative to the longitudinal axis of the tubular housing, and even more preferably at an angle of about 40° to 45°, although the precise angles at which the mirrors are positioned may vary according to assorted and varied uses or objectives for the device.

While it is contemplated that the fundamental arrangement of light source and dual apertures and reflecting means, as heretofore described, would provide an adequate means for inspecting and viewing a restricted space and, in particular, a restricted space at a distance, it is preferred that the device further comprise at least one lens disposed in one of said paths, i.e. the light path and/or the image path. Importantly, it has been found that when a lens 19 is disposed in the light path and, in particular, when a lens 19 is provided in combination with the light source 18 itself, the light source 18 provides a focused beam of light through the illumination aperture 14, thereby providing better illumination of the specific area to be inspected. In particular, it has been found that a light bulb having a lens integrated therewith works best for the purposes of this invention, namely telescopic inspection or the inspection of restricted spaces at a distance or objects therein. Light bulbs having integral lenses are well known in the art, an example of which is the TL-3 bulb manufactured by GTE Sylvania, such as is found in standard pen light-type flashlights. Because the light rays are focused rather than scattered, not only does the focused light beam provided by such a bulb reduce the incidence of excess light or light diffusion, but it further provides for superior distance illumination and increased visual clarity due to the discrete and accurate direction and projection of light. And because the possibility of light diffusion and the resulting lack of visual clarity increases with the distance at which inspection is desired, the focused light beam constitutes an important advantage when the inspection of long, narrow spaces is desired, such as the inspection of the interior of a wall, one of the many anticipated uses for the instant device.

Likewise, when a lens is disposed in the image path, the light and the image received from the restricted space are, consequently, enhanced. In especially preferred embodiments, in addition to the lens 19 integrated with the light source 18, the optical device of this invention comprises a compound lens system 20. As illustrated in drawings, the compound lens system 20 is positioned anterior to the viewing aperture 15 and corresponding mirror 17. Such compound lens systems are well known in the art and typically comprise at least two lenses 21, 22. When the image is received through the viewing aperture 15, it is reflected off of the corresponding mirror 17 and through the compound lens system 20 to the eye of the observer. The compound lens system 20 functions to alter and enhance the image, by magnifying, widening and/or focusing it, thus making the resulting image clearer and more easily discernable to the observer. As stated earlier, mirrors 16, 17 which are curved, as opposed to planar, would also provide an enhanced image or additional means for focusing the desired objects or space and, thus, an available alternative to employing lenses.

The optical device of this invention has a further advantage in that it may be used to inspect numerous variations of restricted spaces, from narrow to wide, and at various distances. The device is particularly suitable for viewing narrow spaces due to the fact that the illumination and viewing apertures are located adjacent to the distal end of the device which is the end first inserted into the restricted space. Furthermore, while it is contemplated that the device could utilize a remote power supply, it is preferred that the device comprises its own power supply, thus lending to the portability of the device. Importantly and advantageously, the power supply 23 is located at the sight end of the device, thereby not interfering with the ability of the aperture portion of the device to be inserted into confined areas. The device further comprises conducting means 25 disposed along the inner wall surface of the housing 11 and connecting the power supply 23 to the light source 18, and a switch 26 to control the power supply 23.

Figure 4:
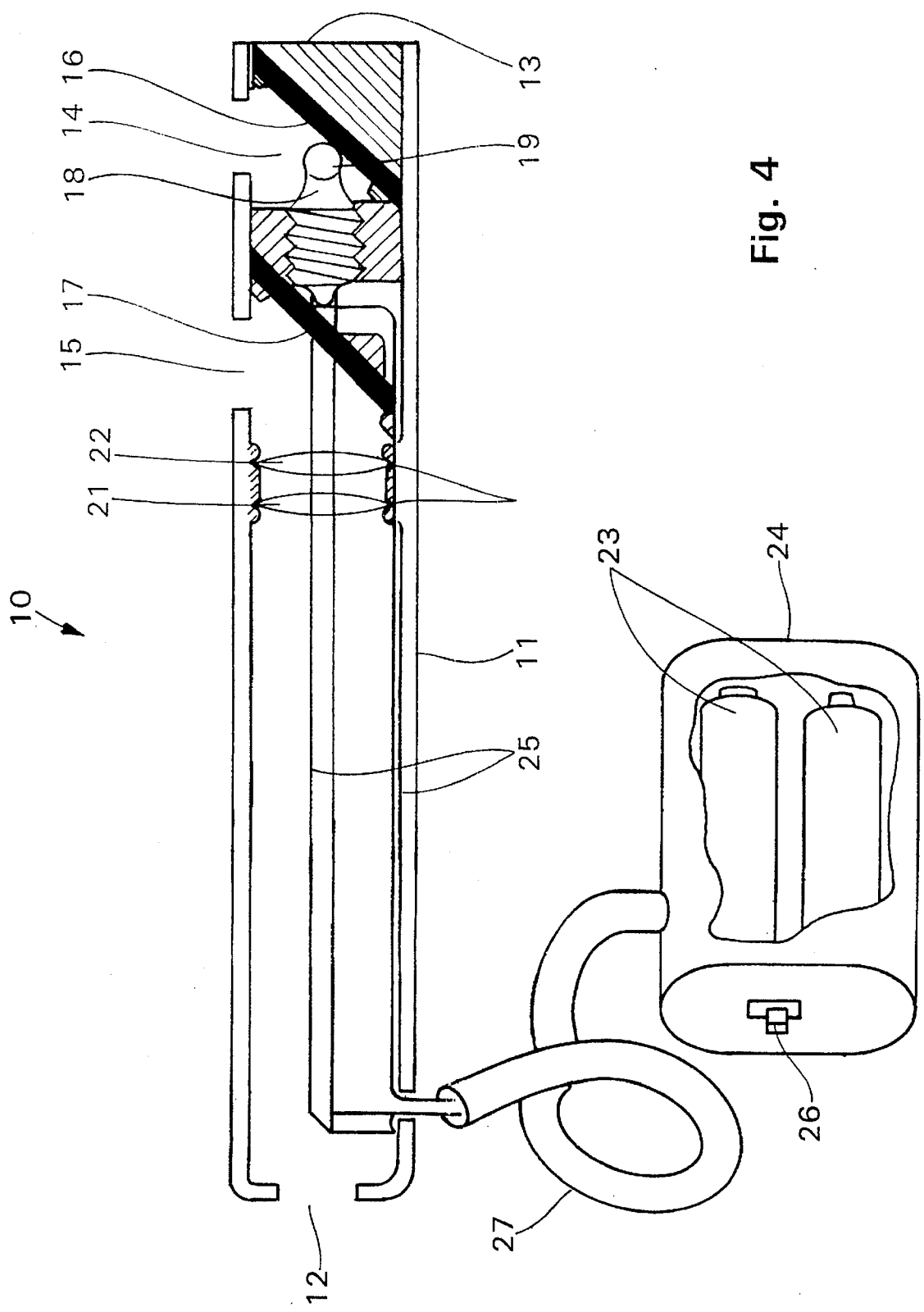
FIG. 4 is a sectional view of the subject optical device, illustrating an alternative embodiment with respect to the encasement means for the power source.

In preferred embodiments, the optical device comprises means for encasing the power supply 23. The encasement means 24 is preferably positioned adjacent to the sight end 12 and sized to accommodate the independent power supply 23, for example, one or more standard batteries. It is contemplated, however, that in an alternative embodiment, as shown in FIG. 4, the encasement means 24 can be located not adjacent to, but separate and at a distance from, the tubular housing 11 of the device. Such an embodiment would further comprise connecting means, such as a flexible power cord 27, disposed between the housing 11 and the power supply encasement means 24. Such a configuration would provide for control over the power supply 23 without the need to physically access the housing 11 of the device, and would further provide for maintaining the narrow dimensions of the device without any interference from the power supply 23 or encasement means 24 therefor, for instance, if the restricted space was particularly narrow and yet as deep or deeper than the length of the device. Such a configuration would also make it possible for the power supply 23 to remain at a distance from the housing and inspection area, for example, on the observer's work belt, while the observer is utilizing the device for inspection.

The optical device of this invention is preferably of compact size and portable in nature, so as to be carried with ease, such as on a work belt, or in a pocket or tool box. It is contemplated that, for additional convenience, the device may further comprise a fastening mechanism, such as a belt clip, for readily carrying the device. Further, the device is preferably of a simple design and construction, thereby providing for relatively quick and inexpensive manufacture. In particular, the optical device of this invention is preferably manufactured from plastic or other similarly non-conductive material, with the individual parts of the device being secured therein by various retaining means, as well known in the art. In addition, because the device is bilaterally symmetrical along its longitudinal axis, it lends itself to simple manufacture in two equal parts. One advantage to such construction is that the two parts are readily separable, so as to provide for the easy access to the interior of the device, for example, for the replacement of the light bulb.

What is claimed is:

1. An optical device for illuminating and optically inspecting the interior of a restricted space, comprising:

a. an elongated tubular housing comprising a proximal sight end having an opening to which viewing means is to be applied, and a distal end;

b. first and second apertures disposed in end to end relationship in an outer surface of said housing, said first aperture being an illumination aperture adjacent to said distal end, and said second aperture being a viewing aperture anterior to said first aperture;

c. first and second reflecting means disposed within said housing, said reflecting means corresponding with and located beneath said first and second apertures, each being angularly disposed and positioned in substantially parallel planes, and each having a reflective surface facing said proximal end; and d. a light source capable of providing a beam of light and located between said first and second reflecting means, said first reflecting means being positioned to project said light beam in a light path from said light source through said illumination aperture into said restricted space, and said second reflecting means being positioned to project the illuminated image in an image path from said restricted space through said viewing aperture and through said sight end.

2. The optical device of claim 1, wherein said light source comprises a light bulb.

3. The optical device of claim 1, wherein said device further comprises at least one lens disposed in one of said paths.

4. The optical device of claim 3, wherein said light source comprises a light bulb.

5. The optical device of claim 4, wherein said at least one lens is disposed in said light path and integrated with said light bulb, so as to provide a focused light beam from said light bulb through said illumination aperture into said restricted space.

6. The optical device of claim 3, wherein said at least one lens is disposed in said image path and comprises a compound lens system positioned anterior to said first and second reflecting means and transversely to said housing.

7. The optical device of claim 1, wherein said first and second reflecting means comprises two mirrors.

8. The optical device of claim 7, wherein said mirrors have planar reflective surfaces disposed in said paths.

9. The optical device of claim 7, wherein said mirrors have concave reflective surfaces disposed in said paths.

10. The optical device of claim 1, wherein said first and second reflecting means are positioned at an angle of about 35° to 55° relative to a longitudinal axis of said housing.

11. The optical device of claim 10, wherein said reflecting means are positioned at an angle of about 40° to 45° relative to the longitudinal axis of said housing.

12. The optical device of claim 1, wherein said device further comprises means for encasing a power supply.

13. The optical device of claim 12, wherein said encasement means is positioned at the sight end of said device and adjacent to said housing.

14. The optical device of claim 12, wherein said encasement means is attached to the housing of said optical device by connecting means disposed between said housing and said encasement means.

15. The optical device of claim 12, wherein said device further comprises a power supply.

16. The optical device of claim 15, wherein said power supply comprises at least one battery.

17. The optical device of claim 15, wherein said power supply comprises a remote power supply.

18. The optical device of claim 1, wherein said device is adapted to be inserted into and to illuminate and optically inspect the interior of a wall.

* * * * *